(12) United States Patent
Sturm et al.

(10) Patent No.: US 8,648,189 B2
(45) Date of Patent: Feb. 11, 2014

(54) METHOD FOR THE PREPARATION OF RIVORAXABAN

(75) Inventors: Hubert Sturm, Kundl (AT); Dominic De Souza, Kundl (AT); Kerstin Knepper, Kundl (AT); Martin Albert, Kundl (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 13/577,441

(22) PCT Filed: Feb. 10, 2011

(86) PCT No.: PCT/EP2011/051920
§ 371 (c)(1),
(2), (4) Date: Nov. 13, 2012

(87) PCT Pub. No.: WO2011/098501
PCT Pub. Date: Aug. 18, 2011

(65) Prior Publication Data
US 2013/0184457 A1   Jul. 18, 2013

(30) Foreign Application Priority Data

Feb. 10, 2010 (EP) .................................. 10153160

(51) Int. Cl.
| C07D 419/10 | (2006.01) |
| C07D 419/14 | (2006.01) |
| C07D 333/22 | (2006.01) |

(52) U.S. Cl.
USPC ............................. 544/137; 544/146; 549/72

(58) Field of Classification Search
None
See application file for complete search history.

(56) References Cited

FOREIGN PATENT DOCUMENTS

| WO | 01/47919 A1 | 7/2001 |
| WO | 2004/060887 A1 | 7/2004 |
| WO | 2004/101557 A1 | 11/2004 |

OTHER PUBLICATIONS

Written Opinion and International Search Report issued May 12, 2011 in parent international application.
Kitchin J, et. al., Synthesis and Structure—Activity Relationships of a Series of Penicillin Derived HIV Proteinase Inhibitors: Heterocyclic Ring Systems Containing P1' and P2' Substituents, J. Med. Chem. (1994), vol. 37, pp. 3707-3716.
International Preliminary Report on Patentability mailed Feb. 10, 2012 in parent international application.
Canadian Office Action issued Sep. 16, 2013 in Canadian Application No. 2,788,755.

*Primary Examiner* — Michael Barker
(74) *Attorney, Agent, or Firm* — Jeffrey S. Melcher; Manelli Selter PLLC

(57) ABSTRACT

The present invention relates to the use of a compound having the formula (II) for the preparation of a compound having the formula (V). Methods of preparing the compound having the formula (V) using the compound having the formula (II) are also described. Individual reaction steps as well as intermediates are additionally claimed.

19 Claims, 4 Drawing Sheets

METHOD FOR THE PREPARATION OF RIVORAXABAN

FIELD OF THE INVENTION

The present invention relates to the use of a compound having the formula (II) for the preparation of a compound having the formula (V). Methods of preparing the compound having the formula (V) using the compound having the formula (II) are also described. Individual reaction steps as well as intermediates are additionally claimed.

BACKGROUND OF THE INVENTION

The compound having the formula (V) has been disclosed in WO 01/47919.

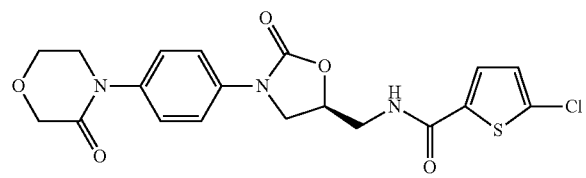
(V)

It is also known as rivaroxaban and is marketed in a number of countries under the trade designation Xarelto.

The compound having the formula (V) acts as an inhibitor of clotting factor Xa and may be used as an agent for the prophylaxis and/or treatment of thromboembolic disorders, especially myocardial infarction, angina pectoris (including unstable angina), reocclusions and restenoses after angioplasty or aortocoronary bypass, stroke, transient ischemic attacks, peripheral arterial occlusive diseases, pulmonary embolisms or deep venous thromboses.

One method for preparing the compound having the formula (V) is disclosed in WO 2004/060887. The method disclosed therein uses a brominated compound

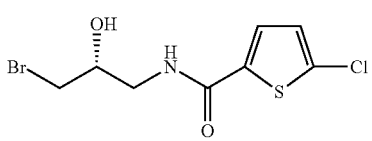 [SMILES: O=C(NC[C@@H](O)CBr)c1ccc(Cl)s1]

as an intermediate which is prepared using hydrobromic acid at elevated temperatures. Hydrobromic acid is corrosive and is therefore undesirable.

It was therefore an object of the present invention to provide a method of preparing the compound having the formula (V) which does not require the use of hydrobromic acid.

It was a further object of the present invention to provide a method of preparing the compound having the formula (V) which is simpler and faster.

It was yet another object of the present invention to provide a method of preparing the compound having the formula (V) which has a higher yield and results in a compound having the formula (V) which has a higher purity.

SUMMARY OF THE INVENTION

The following compounds are referred to in the present invention:

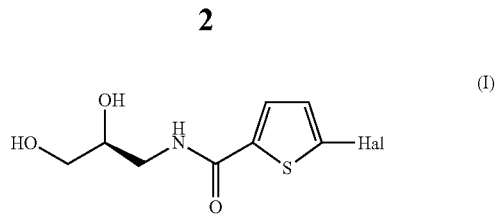
(I)

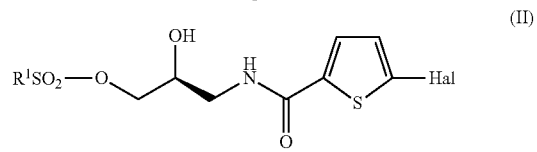
(II)

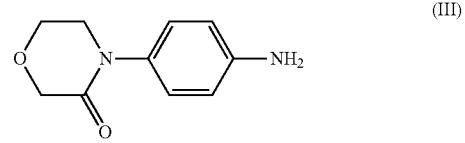
(III)

(IV)

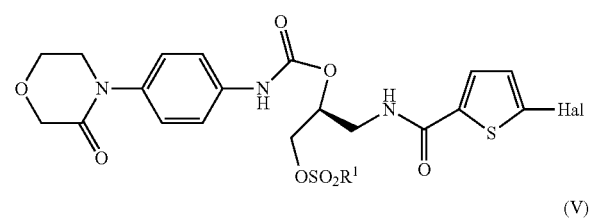
(V)

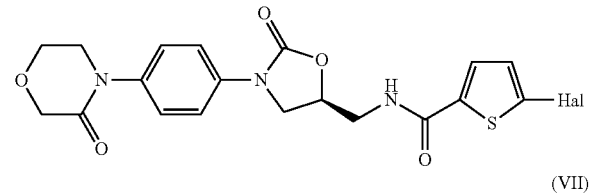
(VI)

(VII)

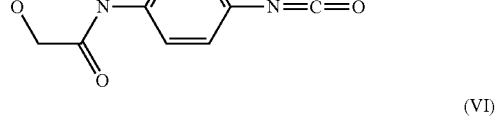
(VIII)

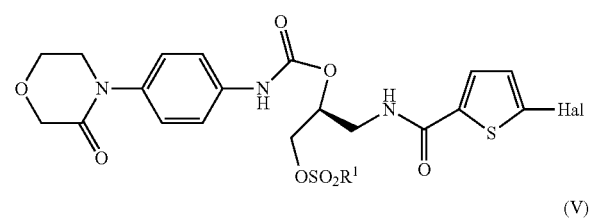
(IX)

The following definitions apply throughout the application unless defined otherwise.

$R^1$ is selected from the group consisting of $C_{1-4}$ alkyl groups and a phenyl group optionally substituted with a $C_{1-4}$ alkyl group. Preferably $R^1$ is selected from the group consisting of methyl, phenyl and tolyl, more preferably $R^1$ is tolyl.

Hal is a halogen atom such as F, Cl, Br or I or a pseudohalogen such as CN. Preferably Hal is Cl.

$R^2$ is a $C_{1-6}$ alkyl group or a benzyl group. Preferably $R^2$ is a $C_{1-4}$ alkyl group, more preferably $R^2$ is methyl.

X is a suitable leaving group such as a halogen atom (such as F, Cl, Br or I) or a pseudohalogen (such as CN). In the case of $R^1SO_2X$ X can also be a carboxylate such as an anhydride. Preferably X is a halogen such as Cl.

Phosgene is $COCl_2$. Phosgene equivalents can be employed in the methods of the present invention instead of phosgene itself. These include trichloromethyl chloroformate ("diphosgene") and bis(trichloromethyl) carbonate ("triphosgene") as well as CO equivalents such as 1,1-carbonyldiimidazol.

In one embodiment the present invention refers to the use of a compound having the formula (II) for the preparation of the compound having the formula (V).

In a further embodiment the present invention relates to a method for the preparation of the compound having the formula (V) wherein the method comprises reacting (i) a compound having the formula (II); (ii) a compound having the formula (III) and (iii) phosgene or an equivalent thereof.

In yet another embodiment the invention pertains to a method for preparing a compound having the formula (II) wherein a compound having the formula (I) is converted to the compound having the formula (II).

Subject matter of the present invention is also a method for preparing a compound having the formula (VI) wherein a compound having the formula (II) is reacted with a compound having the formula (III).

In an additional embodiment, the invention relates to a method for preparing a compound having the formula (IV) wherein a compound having the formula (II) is first reacted with phosgene or an equivalent thereof and the reaction product thereof is subsequently reacted with a compound having the formula (III).

A method for preparing a compound having the formula (V) wherein a compound having the formula (IV) is converted to the compound having the formula (V) is also subject matter of the present invention.

In another embodiment the present invention relates to a method for preparing a compound having the formula (V) wherein a compound having the formula (II) is reacted with a compound having the formula (VIII).

A method comprising the step of reacting a compound having the formula (II) with a compound having the formula (VII) to provide a compound having the formula (V).

The present invention further relates to a method comprising the step of converting a compound having the formula (II) into a compound having the formula (IX).

In another embodiment of the invention a method is disclosed which comprises the step of reacting a compound having the formula (IX) with a compound having the formula (VII) to obtain a compound having the formula (V).

In a further embodiment the present invention relates to a method for preparing a compound having the formula (V) wherein a compound having the formula (II) is converted into a compound having the formula (IX) and the compound having the formula (IX) is reacted with a compound having the formula (VII).

Compounds having the formulae (II), (IV), (VII) and (IX) are also embodiments of the invention.

DETAILED DESCRIPTION OF THE INVENTION

Figure 1:
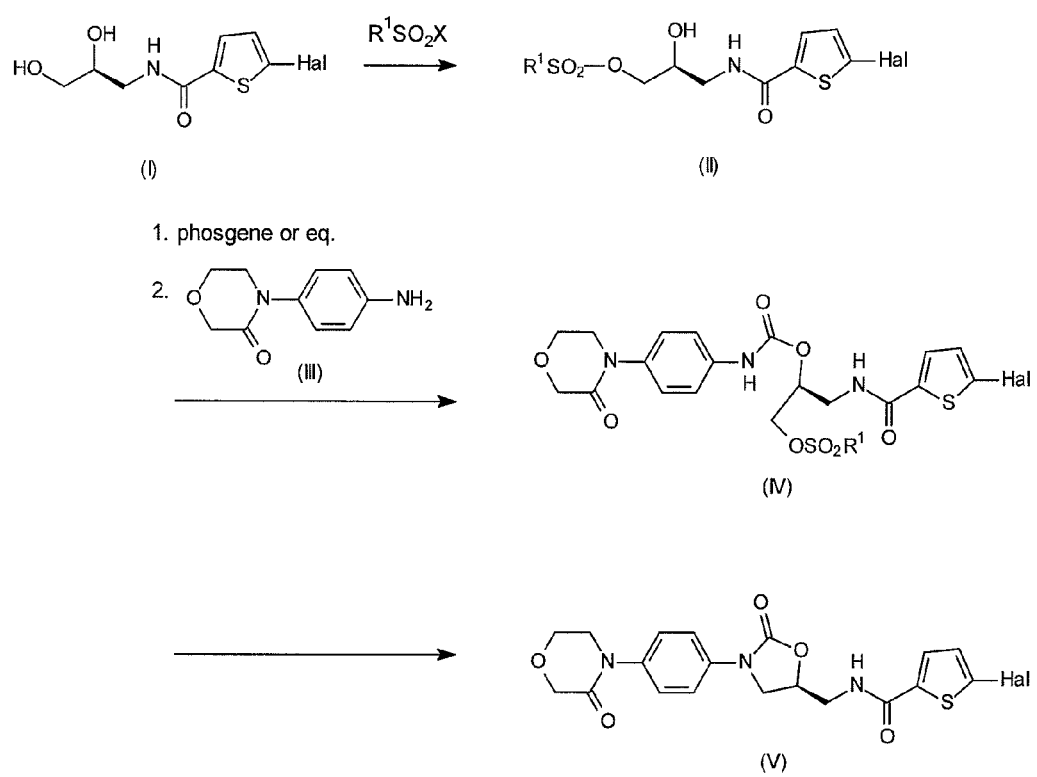
FIGS. 1 to 4 summarize reaction schemes according to the invention.
Figure 2:
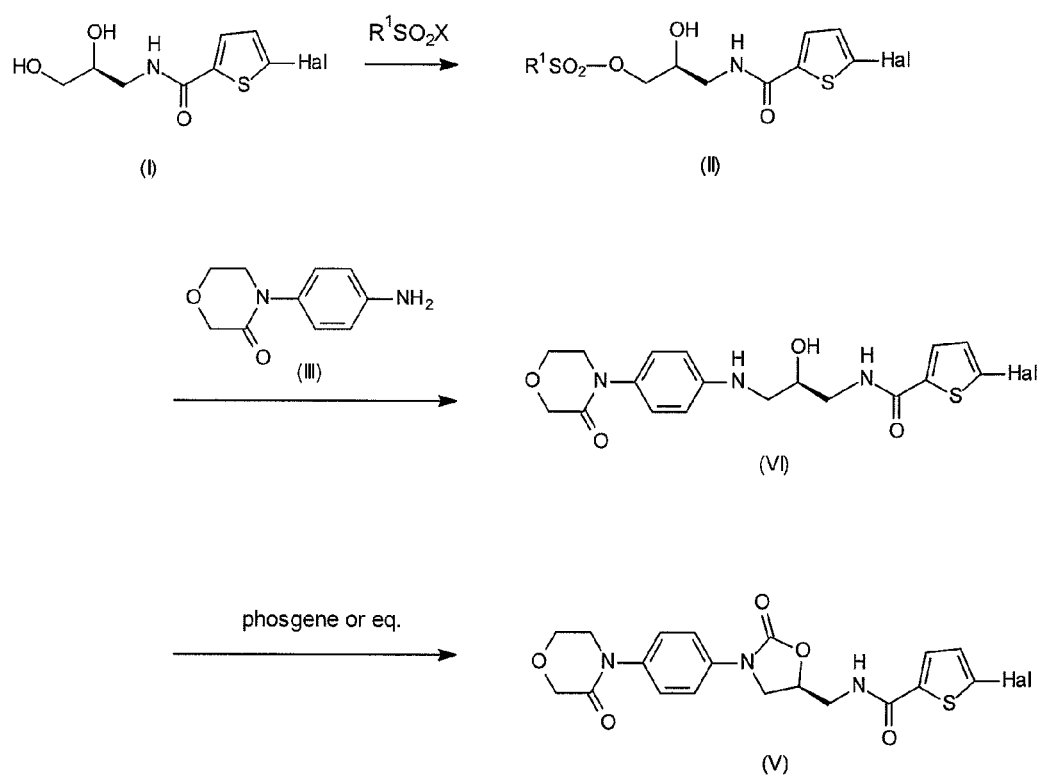
Figure 3:
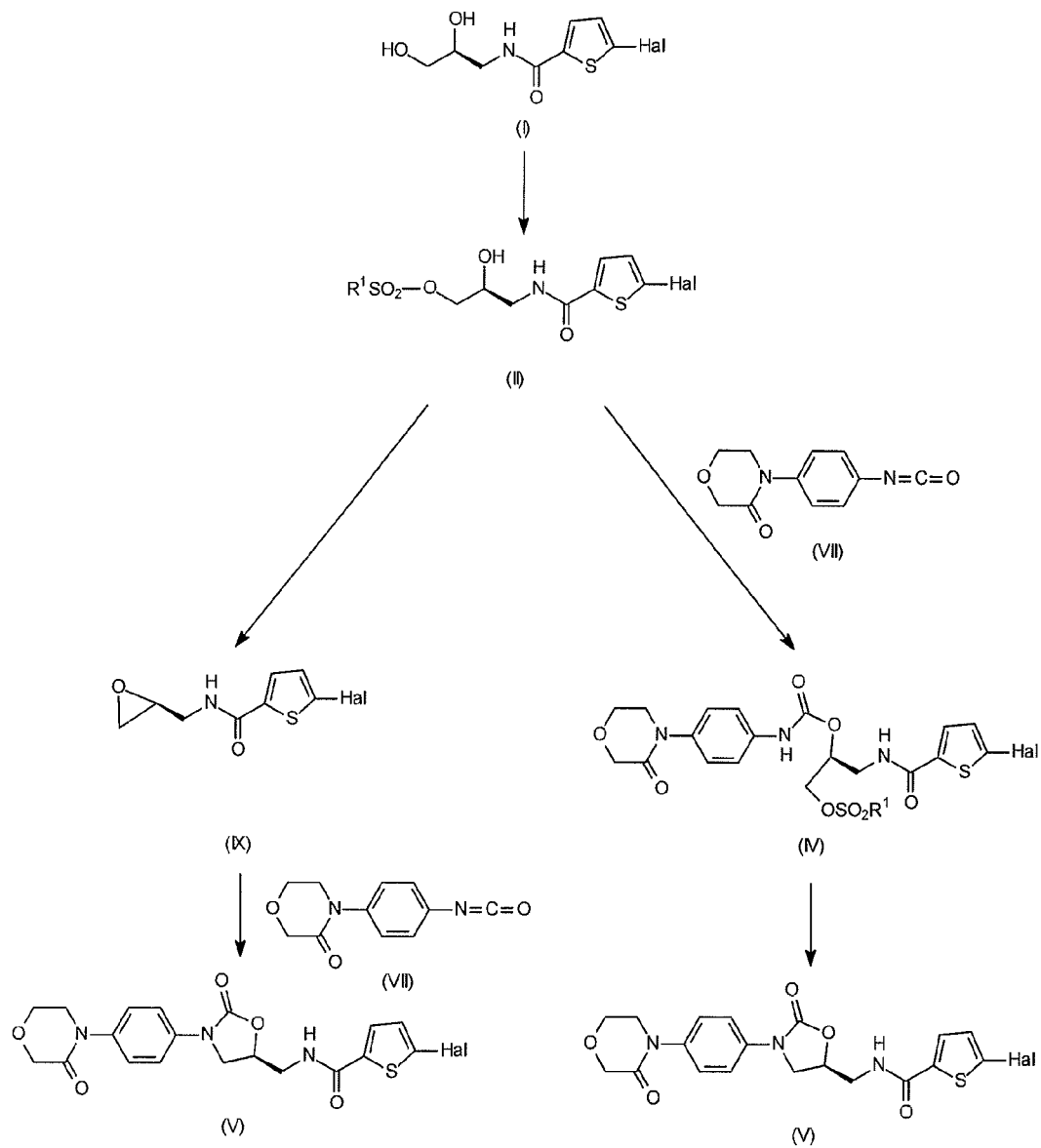
Figure 4:
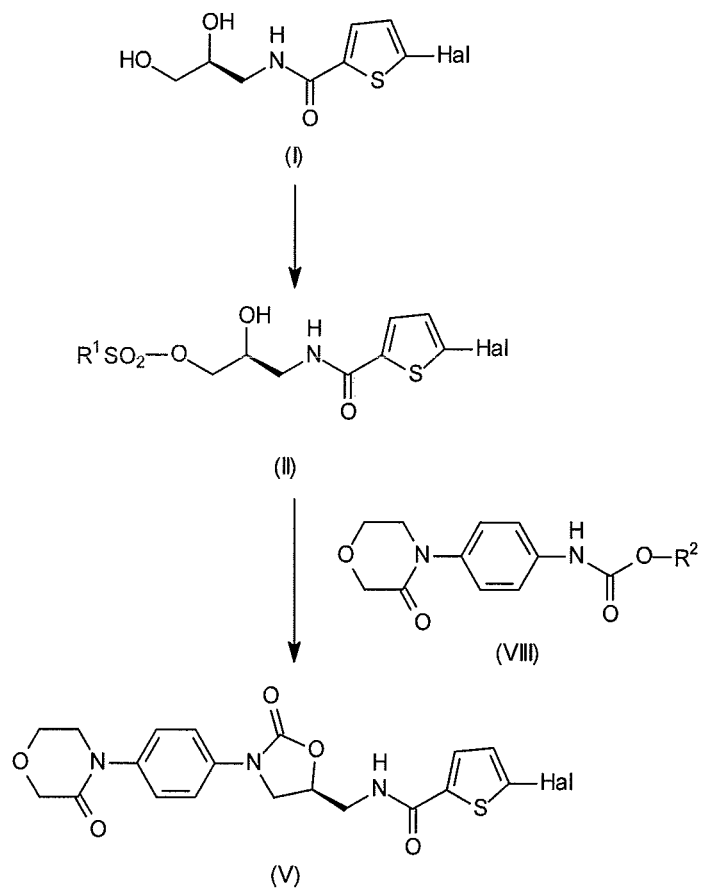

Preparation of the Compound Having the Formula (I):

Examples of the compound having the formula (I) are known. They can be prepared by conventional methods such as those which are analogous to the method which is disclosed in WO 2004/060887. For example, (2S)-3-aminopropane-1,2-diol can be reacted with 5-halogenothiophene-2-carbonyl halide under basic conditions.

Preparation of the Compound Having the Formula (II) from the Compound Having the Formula (I):

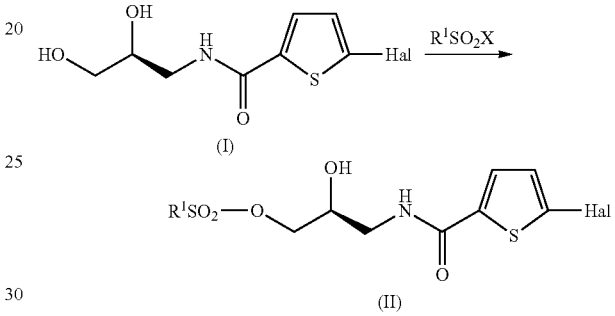

The compound having the formula (II) can be prepared from a compound having the formula (I). The reaction can be conducted using any suitable reaction conditions. Typically the compound having the formula (I) will be reacted with a compound having the formula $R^1SO_2$—X.

The molar ratio of compound having the formula $R^1SO_2$—X to the compound having the formula (II) is preferably in the range of about 1.0 to about 1.5, more preferably about 1.0 to about 1.1.

The solvent used in this reaction step will typically be a polar aprotic solvent, which e.g. can be selected from nitrile-type solvents (such as acetonitrile), amides (such as DMF), sulfones (such as sulfolane), cyclic amines (such as pyridine) as well as mixtures thereof. A polar solvents such as halogenated hydrocarbons (such as dichloromethane) or aromatic solvents (such as toluene) or mixtures thereof can also be used. The solvent is preferably a nitrile-type solvent such as acetonitrile because it is easy to crystallize the compound having the formula (II) from this solvent.

The reaction can be conducted at any suitable temperature. Typical reaction temperatures range from about −20° C. to about 100° C., preferably about 0° C. to about 50° C. More preferably the reaction is conducted at room temperature (e.g., 20 to 25° C.).

The reaction can be conducted in the presence of an auxiliary which facilitates the regioselective reaction of the compound having the formula $R^1SO_2$—X with the primary alcohol. Such auxiliaries include organotin compounds such as dialkyltin oxide (wherein alkyl is e.g., $C_{1-6}$ alkyl). A preferred auxiliary is dibutyltin oxide. The molar ratio of auxiliary to the compound having the formula $R^1SO_2$—X is preferably in the range of about 0.01 to about 0.10, more preferably about 0.01 to about 0.05.

The presence of the auxiliary is preferred because it can significantly reduce the amount of by-product in which both of the hydroxy groups of the compound having the formula (I) have reacted with the compound having the formula $R^1SO_2$—X. This improves the yield of the desired compound having the formula (II) as well as its purity. Furthermore, it has been surprisingly found that the reaction time can be significantly reduced if an auxiliary is used. Due to the reduced amount of by-products the purification of the compound having the formula (II) is also simplified.

The reaction can be conducted in the presence of a base. Typical examples of bases include organic and inorganic bases such as amine compounds. Amine compounds such as tri($C_{1-4}$ alkyl)amines are preferably used. They can be employed in a molar ratio in the range of about 1.0 to about 1.5, preferably about 1.0 to about 1.2 compared to the compound having the formula $R^1SO_2$—X.

The duration of the reaction will depend on the other reaction conditions chosen and can range from about 0.5 h to about 5 h, more typically from about 1 h to about 2 h.

After the reaction has been completed, the compound having the formula (II) will be usually isolated from the reaction mixture. One method of isolating the compound having the formula (II) is to induce crystallization by adding water and adjusting the pH to be acidic. The crystals can then be separated from the solvent by conventional methods such as filtration, centrifugation etc. and optionally be washed and/or dried.

Compared to the reaction described in WO 2004/060887 in which a brominated compound is prepared by reacting N—((S)-2,3-dihydroxypropyl)-5-chlorothiophene-2-carboxamide with hydrobromic acid, the instant method is advantageous because it is possible to conduct the reaction at room temperature. Furthermore, the yield is surprisingly higher. In addition, the isolation of the desired compound having the formula (II) is significantly simplified because it is not necessary to remove the reaction solvents first by distillation and then to induce crystallization using a different solvent mixture as described in WO 2004/060887. Rather crystallization can be induced directly in the reaction solvent. Because it is possible to use a single solvent instead of two different solvent mixtures, recycling and disposal of the solvents are also facilitated. The duration of the reaction can also be shorter using the process according to the invention.

The compound having the formula (V) can be obtained by reacting the compound having the formula (II), a compound having the formula Op and phosgene or an equivalent thereof. The sequence of the reaction steps is not particularly limited. In one embodiment, the compound having the formula (II) is first reacted with the compound having the formula (III) to obtain a compound having the formula (VI) and then the compound having the formula (VI) is reacted with phosgene or an equivalent thereof to obtain the compound having the formula (V). In an alternative embodiment, the compound having the formula (II) is first reacted with phosgene or an equivalent thereof; the reaction product thereof is subsequently reacted with a compound having the formula (III) to obtain a compound having the formula (IV) and the compound having the formula (IV) is converted to the compound having the formula (V). These reactions can be conducted as a one pot reaction. Alternatively it is possible to isolate the intermediates and optionally purify them before the second reaction step is conducted.

Preparation of the Compound Having the Formula (IV) from the Compound Having the Formula (II):

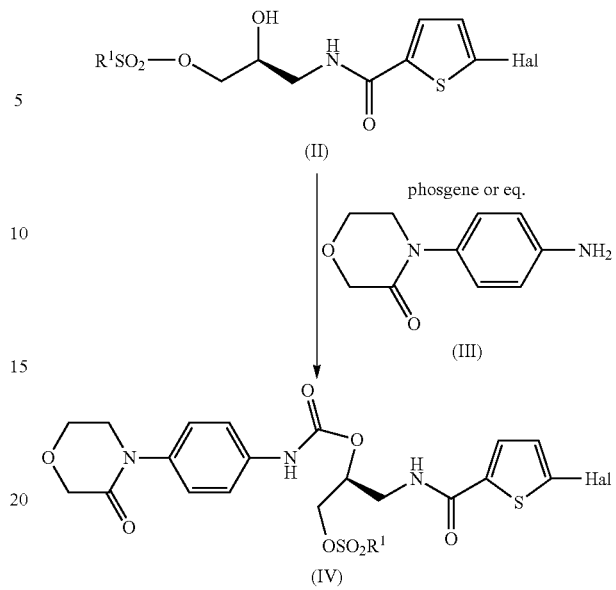

The compound having the formula (II) is first reacted with phosgene or an equivalent thereof and the reaction product thereof is subsequently reacted with a compound having the formula (III) to obtain a compound having the formula (IV).

The reaction of the compound having the formula (II) with phosgene can be conducted using any suitable conditions. The conditions will differ depending on whether phosgene or a phosgene equivalent is employed. Typically the compound having the formula (II) will be provided in a suitable solvent. The solvent will usually be a polar solvent. Examples of suitable solvents include halogenated hydrocarbons (such as dichloromethane), ethers (such as THF), amides (such as NMP), mixtures of hydrocarbons and alcohols (such as mixtures of toluene and $C_{1-4}$ alcohols) and nitriles (such as acetonitrile). Mixtures of the foregoing solvents are also possible. Preferred solvents are halogentated hydrocarbons and ethers.

The phosgene or equivalent thereof will typically be used in a molar ratio of the compound having the formula (II) to phosgene in the range of about 1.0 to about 1.5, more preferably about 1.0 to about 1.1. If phosgene equivalents are used, the molar ratio will be calculated based on the amount of phosgene equivalents which are provided by these compounds.

In order to facilitate the reaction it can be conducted in the presence of a base. Examples of suitable bases include organic amines, preferably organic cyclic amines such as pyridine. They can be employed in a molar ratio in the range of about 2.0 to about 5.0, preferably about 2.5 to about 3.5 compared to the compound having the formula (II).

The reaction temperature is not particularly limited. It will typically be in the range of about −60° C. to about 60° C., preferably about −40° C. to about 20° C.

The reaction will usually be completed with about 1 min to about 1 h, more typically about 5 min to about 30 min.

After the reaction with phosgene or an equivalent thereof has been completed, the intermediate can be isolated. Alternatively and preferably the subsequent reaction to the compound having the formula (IV) can be conducted without isolation of the intermediate.

The reaction of the intermediate with the compound having the formula (III) can be conducted in the same solvent as mentioned above with respect to the phosgene reaction.

The compound having the formula (III) is preferably added in an amount, so that the molar ratio of the compound having the formula (III) to the compound having the formula (II) is in the range of about 1.0 to about 1.5, more preferably about 1.0 to about 1.1.

If desired or necessary, the reaction can be conducted under an inert gas atmosphere.

The reaction of the intermediate with the compound having the formula (III) can be, e.g., conducted at a temperature in the range of about −40° C. to about 50° C., more preferably about 0° C. to about 30° C.

The reaction will typically take about 1 h to about 24 h, more typically about 1 h to about 2 h.

After the reaction has been completed, the compound having the formula (IV) can be isolated and/or purified, if desired. Conventional purification methods such as evaporation of the solvent can be employed. This step has the advantage of an additional purification by crystallization which improves the yield and purity in a subsequent synthetic step.

Preparation of the Compound Having the Formula (V) from the Compound Having the Formula (IV):

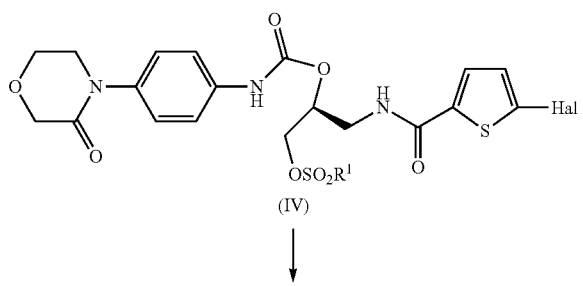

(IV)

reaction which is not particularly limited. In one embodiment the compound can be provided in a solvent. Examples of possible solvents include protic and aprotic organic solvents. Preferred solvents include ether solvents (such as THF), nitrile solvents (such as acetonitrile) and alcohols (such as $C_{1-4}$ alcohols, e.g. isopropanol).

The reaction is typically conducted in the presence of a base to facilitate the cyclization. Examples of suitable bases include organometallic and organic bases. Preferred bases are, e.g., organolithium compounds (such as lithium bis(trimethylsilyl)amide (LiHMDS) and lithium diisopropylamide (LDA)), hydrides and alcoholates (such as alkali or alkali earth $C_{1-6}$ alkoxides). The base will be usually present in a molar ratio of base to compound having the formula (IV) in the range of about 1.0 to about 1.5, preferably about 1.0 to about 1.1.

If desired or necessary, the reaction can be conducted under an inert gas atmosphere.

The reaction can be conducted at any suitable temperature. The temperature will typically be in the range of about −40° C. to about 40° C., preferably about −10° C. to about 30° C.

The reaction will usually be completed with about 0.5 h to about 2 h, more typically about 0.5 h to about 1 h.

The compound having the formula (V) can be easily isolated from the reaction mixture by conventional methods such as evaporation of the solvent. Further purification steps such as washing, drying and/or recrystallization will conducted by a person skilled in the field according to his specific desires.

Preparation of the Compound Having the Formula (VI) from the Compound Having the Formula (II):

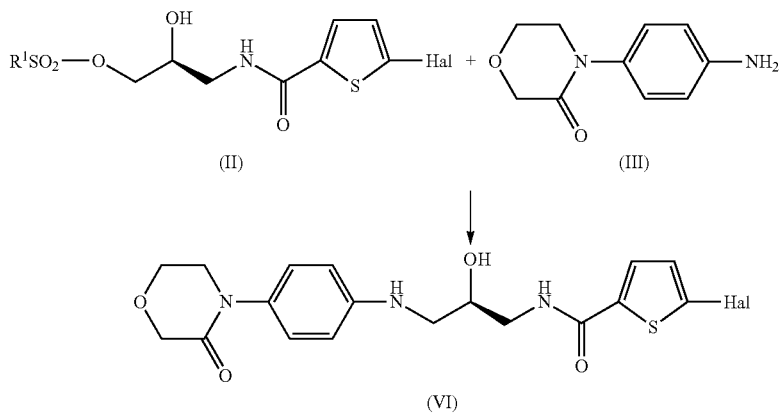

-continued

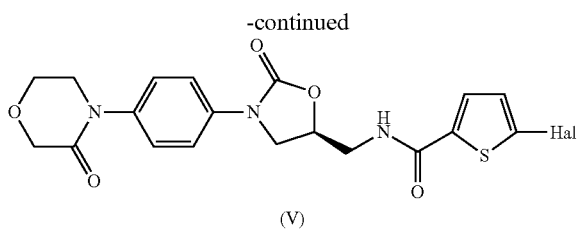

(V)

The method to convert the compound having the formula (IV) to the compound having the formula (V) is a cyclization The compound having the formula (II) can be reacted with a compound having the formula (III) to render the compound having the formula (VI) using any suitable method.

The molar ratio of the compound having the formula (II) to the compound having the formula (III) can be chosen suitably and will usually be in the range of about 1.0 to about 1.5, preferably about 1.0 to about 1.2.

According to one embodiment the reaction can be conducted in a solvent. Examples of typical solvents for this step include hydrocarbons (such as toluene) and nitriles (such as acetonitrile).

The presence of a base can assist the reaction. Illustrative examples of suitable bases include organic bases (such as tri($C_{1-6}$alkyl)amines and collidine) and inorganic bases (such as alkali hydroxides). The base can be added in an amount which is, e.g., in the range of about 0.8 to about 1.5 based on the amount of the compound having the formula (II) (mol: mol).

The reaction temperature can vary in broad ranges. Typical temperatures will be in the range of about 30° C. to about 200° C., more typically about 70° C. to about 120° C.

The reaction will usually proceed for about 1 h to about 8 h, for example about 2 h to about 6 h.

The method for isolating and/or purifying the compound having the formula (VI) are not restricted and can be chosen from conventional methods.

Preparation of the Compound Having the Formula (V) from the Compound Having the Formula (VI):

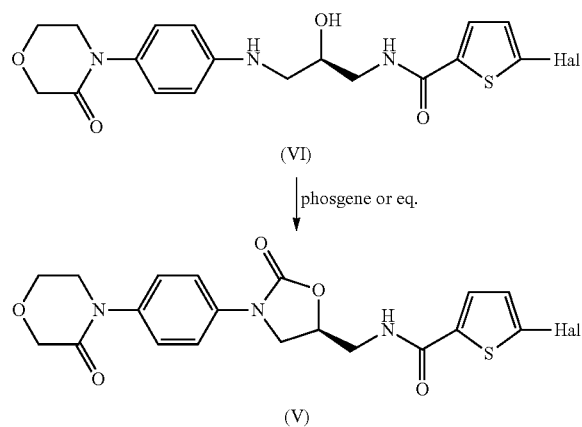

The compound having the formula (VI) can be reacted with phosgene or an equivalent thereof to prepare the compound having the formula (V).

The molar ratio of phosgene to the compound having the formula (VI) will be chosen suitably. The molar ratio will typically be in the range of about 1 to about 5, preferably about 1 to about 2, more preferably about 1.0 to about 1.3. If phosgene equivalents are used, the molar ratio will be calculated based on the amount of phosgene equivalents which are provided by these compounds.

The solvent for this reaction step can be chosen from a wide range of solvents. Possible illustrative examples include aprotic organic solvents, preferably hydrocarbons (such as toluene), nitriles (such as acetonitrile) and ethers (such as THF).

The reaction can proceed at any suitable temperature. Specific examples include a temperature in the range of about 20° C. to about 150° C., preferably from about 30° C. to about 130° C., more preferably about 75° C. to about 120° C.

The duration of this reaction step will often range from about 0.5 h to about 15 h, e.g., from about 2 h to about 3 h.

The method of isolating the compound having the formula (V) (if desired) is not particularly limited. As an example, crystallization can be induced and the resultant crystals can be separated by filtration. If desired, the crystals can be washed, dried and/or recrystallized or treated by any other suitable purification method.

Preparation of the Compound Having the Formula (IX) from the Compound Having the Formula (II):

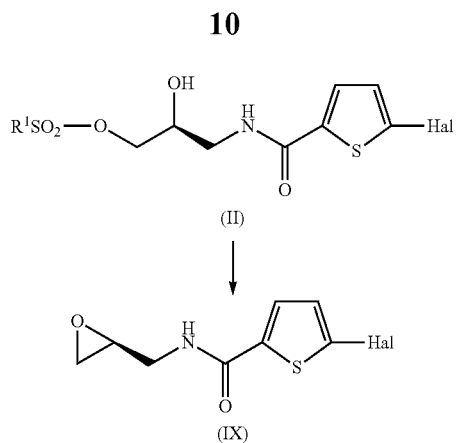

In an alternative embodiment the compound having the formula (IV) can be prepared from the compound having the formula (II) by reaction with a compound having the formula (VII). In the first part of this reaction the compound having the formula (II) is converted to the compound having the formula (IX).

The reaction can proceed under any suitable conditions to conduct the cyclisation reaction. One option is to conduct the cyclisation in the presence of a base. Any suitable base can be used. Examples are inorganic bases (such as carbonates, hydrocarbonates, hydroxides with alkali metals, alkali earth metals or ammonium cations or organic bases (such as $C_{1-8}$ alkoxides of alkali metals and alkaline earth metals). The pH of the reaction mixture should be adjusted, so that it is above 8.

The molar ratio of base to compound having the formula (II) is generally in the range of about 10 to about 1, preferably about 6 to about 1.5.

The reaction will be typically conducted in an polar solvent such as halogenated hydrocarbons (such as methylene chloride), nitriles (such as acetonitrile), ethers (such as THF) and alcohols (such as t-butanol).

The reaction temperature is not particularly limited and can vary, for example, from about −30° C. to about 30° C., preferably about −25° C. to about 25° C.

The duration of the reaction will depend on the other conditions chosen. Typical values are in the range of about 1 h to about 120 h, more typically about 5 h to about 85 h.

The compound having the formula (IX) can be used as such in the further reaction or can be isolated and/or purified using conventional techniques.

Preparation of the Compound Having the Formula (V) from the Compound Having the Formula (IX):

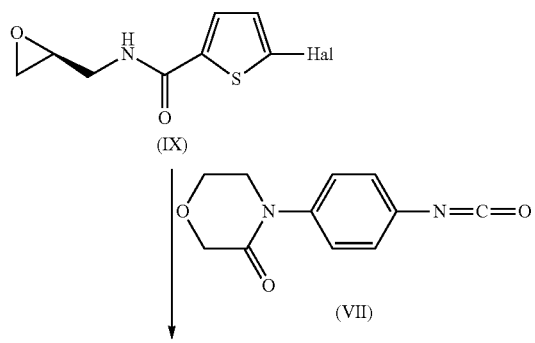

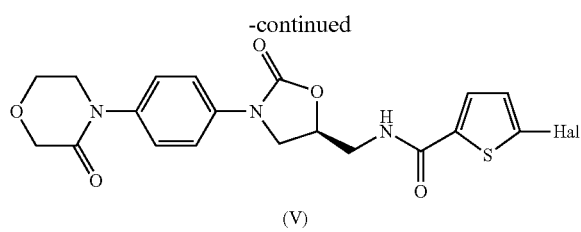

(V)

The compound having the formula (IX) can be reacted with a compound having the formula (VII) to the compound having the formula (V).

The compound having the formula (VII) can be prepared by reacting 4-(4-amino-phenyl)-morpholin-3-one with phosgene or an equivalent thereof. 4-(4-Amino-phenyl)-morpholin-3-one is commercially available or can be prepared as described in WO 2004/060887.

The reaction will be typically conducted in an aprotic solvent. Examples are halogenated hydrocarbons (such as methylene chloride), hydrocarbons (such as toluene) or mixtures thereof.

The reaction temperature is not particularly limited and will typically be in the range of about −40° C. to about 200° C., more typically about 0° C. to about 120° C.

The reaction can be conducted in the presence of an amine (such as mono-, di- or tri($C_{1-4}$ alkyl)amines). The molar ratio of amine to 4-(4-amino-phenyl)-morpholin-3-one is usually from about 1 to about 3, such as about 1.8 to about 2.2.

The reaction between 4-(4-amino-phenyl)-morpholin-3-one and phosgene or an equivalent thereof can be chosen appropriately. Typically reaction times will be from about 0.5 h to about 10 h, such as about 1 h to about 5 h.

The compound having the formula (VII) can be purified (e.g., by crystallization) or used per se in the reaction with the compound having the formula (IX).

The reaction between the compound having the formula (IX) and the compound having the formula (VII) can be conducted under any suitable conditions. It will be typically conducted in an aprotic solvent. Examples of suitable solvents include hydrocarbons (such as toluene), halogenated hydrocarbons (such as methylene chloride) or mixtures thereof.

The reaction can be conducted in the presence of lithium halogenide or tributylphosphine oxide. The molar ratio of lithium halogenide to the compound having the formula (IX) will typically be from about 0.02 to about 0.1, more typically about 0.04 to about 0.06. The molar ratio of tributylphosphine oxide to the compound having the formula (IX) will typically be from about 0.02 to about 0.1, more typically about 0.04 to about 0.06.

The reaction temperature is not particularly limited. It can suitably range from about 0° C. to about 200° C., more suitably from about 20° C. to about 120° C.

The reaction will be typically completed in about 1 h to about 24 h, more typically about 2 h to about 6 h.

The method of isolating the compound having the formula (V) is not particularly limited. It can, for example, be isolated by filtration. If desired, the crystals can be washed, dried and/or recrystallized or treated by any other suitable purification method.

Preparation of the Compound Having the Formula (IV) from the Compound Having the Formula (II)

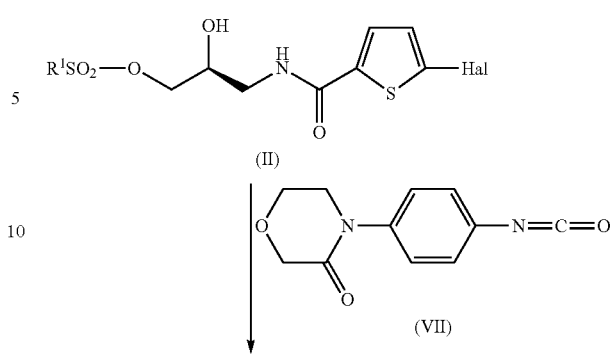

The compound having the formula (II) can be reacted with the compound having the formula (VII) to obtain the compound having the formula (IV).

The reaction will be typically conducted in an aprotic solvent. Examples of suitable solvents include halogenated hydrocarbons (such as methylene chloride), hydrocarbons (such as toluene) and mixtures thereof.

The molar ratio of the compound having the formula (II) to the compound having the formula (VII) will typically be from about 1 to about 1.5, more typically about 1 to about 1.1.

The reaction temperature is not particularly limited and can be in the range of about 0° C. to about 150° C., preferably about 20° C. to about 120° C.

The duration of the reaction can be, for example about 0.5 h to about 24 h, e.g., about 1 h to about 12 h.

The compound having the formula (IV) can be isolated and/or purified or used as such in a further reaction.

The compound having the formula (IV) can be converted into the compound having the formula (V) as explained above.

Preparation of the Compound Having the Formula (V) from the Compound Having the Formula (II):

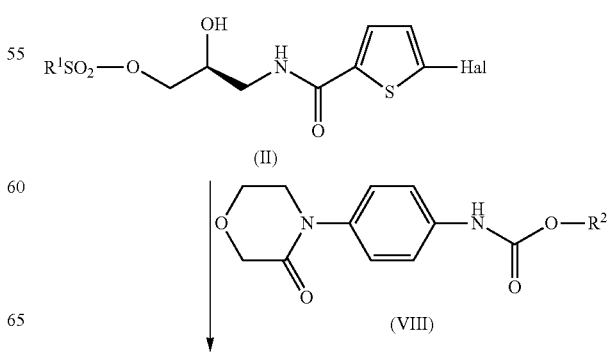

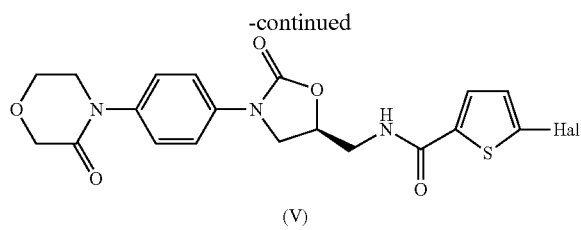

(V)

In a further alternative embodiment, the compound having the formula (II) can be reacted with a compound having the formula (VIII) to prepare the compound having the formula (V).

The compound having the formula (VIII) can be prepared according to any suitable method. One possibility is to prepare it by reacting 4-(4-amino-phenyl)-morpholin-3-one with X—C(O)—O—R².

The reaction will be typically conducted in a solvent. Examples of suitable solvents include hydrocarbons (such as toluene), halogenated hydrocarbons (such as methylene chloride), ketones (such as acetone), nitriles (such as acetonitrile), mixtures of acetone/water, mixtures of acetonitrile/water and mixtures thereof.

The reaction temperature is not particularly limited and can, e.g., be from about −20° C. to about 60° C., more particularly from about −10° C. to about 40° C.

The reaction time can vary and, e.g., be from about 1 h to about 4 h, such as from about 1.5 h to about 2.5 h.

The molar ratio of 4-(4-amino-phenyl)-morpholin-3-one to X—C(O)—O—R² will typically be from about 1 to about 1.5, more typically about 1.0 to about 1.1.

If desired, the reaction can be conducted in the presence of an inorganic or an organic base. Preferred bases are, e.g., sodium bicarbonate and triethylamine. The molar ratio of base to compound having the formula (II) is in the range of about 1.0 to about 3, preferably about 1.0 to about 2.5.

After the reaction has been completed, the compound having the formula (VIII) will be usually isolated from the reaction mixture. One method of isolating the compound having the formula (VIII) is to induce crystallization by adding water. The crystals can then be separated from the solvent by conventional methods such as filtration, centrifugation etc. and optionally be washed and/or dried.

The reaction of the compound having the formula (II) with the compound having the formula (VIII) can be conducted using any suitable conditions. A possible reaction route including acylation, cyclization and deacylation is described in the following.

Acylation:

The compound having the formula (II) can be first reacted with acetic acid anhydride to obtain the corresponding acetyl derivative of the compound having the formula (II). The acylation reaction will be typically conducted in a protic or aprotic solvent. Examples of suitable solvents include halogenated hydrocarbons (such as methylene chloride), hydrocarbons (such as toluene), amides (such as DMF), sulfones (such as sulfolane), aromatic bases (such as pyridine), alcohols (such as isopropanol) and mixtures thereof.

The molar ratio of the compound having the formula (II) to acetic acid anhydride will typically be from about 1 to about 1.5, more typically about 1 to about 1.1.

The reaction temperature is not particularly limited and can be in the range of about −20° C. to about 80° C., preferably about −10° C. to about 50° C.

The duration of the reaction can be, for example about 0.5 h to about 24 h, e.g., about 0.5 h to about 5 h.

The acetyl derivative of the compound having the formula (II) can be purified (e.g., by crystallization) or used per se in the reaction with the compound having the formula (VIII).

Cyclization and Deacylation:

The acetyl derivative of the compound having the formula (II) can be reacted with the compound having the formula (VIII) to obtain the compound having the formula (V).

Examples of suitable solvents include amides (such as DMF and DMAC), ethers (such as THF, methyl-t.-butyl ether), sulfones (such as sulfolane), nitriles (such as acetonitrile), halogenated hydrocarbons (such as methylene chloride), hydrocarbons (such as toluene), alcohols (such as t-butanol and t-amyl alcohol) and mixtures thereof.

The molar ratio of the acetyl derivative of the compound having the formula (II) to the compound having the formula (VIII) will typically be from about 0.7 to about 1.4, more typically about 0.7 to about 1.1.

The reaction is preferably conducted in presence of a base and an alcohol.

Examples of suitable bases include alkoxy compounds having one to seven carbon atoms (such as tert.-butoxides or tert.-amylates of alkali metals or alkaline earth metals), carbonates, trialkylamines, DBU, DBN and phosphacene bases. The molar ratio of the base to the compound having the formula (II) will typically be from about 1 to about 3, more typically about 1.4 to about 2.5.

Examples of suitable alcohols are $C_{1-4}$ alcohols such as methanol, ethanol and isopropanol. The molar ratio of the alcohol to the compound having the formula (II) will typically be from about 0.7 to about 4, more typically about 0.7 to about 2.

The reaction temperature can vary in the range of about −40° C. to about 50° C., more typically about −20° C. to about 30° C.

The reaction will usually proceed for about 2 h to about 24 h, for example about 6 h to about 18 h.

The method of isolating the compound having the formula (V) is not particularly limited. It can, for example, be isolated by filtration. If desired, the crystals can be washed, dried and/or recrystallized or treated by any other suitable purification method.

All of the reactions mentioned above can be conducted at ambient pressure or other pressures such as a pressure in the range of about 50 kPa to about 500 kPa. Typically they will be conducted at ambient pressure.

The present invention is illustrated by the following non-limiting examples.

EXAMPLES

Example 1

4-[4-[(5R)-5-(Chlorothiopheno-2-carboxylic acid ((S)-2,3-dihydroxy-propyl)-amide

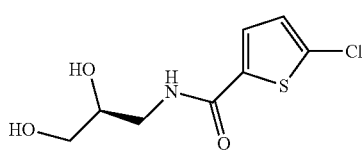 [SMILES: O=C(NC[C@H](O)CO)c1ccc(Cl)s1]

The starting material 4-[4-[(5R)-5-(chlorothiopheno-2-carboxylic acid (S)-2,3-dihydroxy-propylamide was prepared as described in WO 2004/06088.

Example 2

4-[4-[(5R)-5-(Chlorothiopheno-2-carboxylic acid ((S)-2-hydroxy-3-tosyloxy)-propyl)-amide

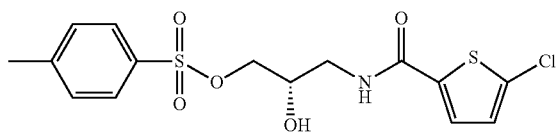 [SMILES: Cc1ccc(S(=O)(=O)OC[C@@H](O)CNC(=O)c2ccc(Cl)s2)cc1]

50.0 g of 4-[4-[(5R)-5-(chlorothiopheno-2-carboxylic acid (S)-2,3-dihydroxy-propylamide (MW=235.69; 1 eq.) and 1.05 g dibutyltin oxide (MW=248.92; 0.02 eq.) were suspended in 900 mL of acetonitrile and refluxed for one hour. Then the suspension was cooled to 22° C. and 27.7 g triethylamine (MW=101.19; 1.1 eq.) were added. Then 41.6 g tosylchloride (MW=190.65; 1.03 eq.) were added within two minutes and the reaction mixture was stirred at 22° C. After stirring for 90 minutes at this temperature the reaction mixture was added within 15 minutes into 4000 mL of water at pH 2.0 by adjusting the pH by addition of 6 M hydrochloric acid. The resulting crystal suspension was stirred at 22° C. for 30 minutes and then cooled to 0° C. After stirring for 1 hour at this temperature the suspension was filtered, the filter cake was washed with 200 mL of cold water and 1 L of toluene. The wet product was dried at 30° C. in vacuo to yield 68.5 g of the title compound in the form of a crystalline powder (approx. 85.5% of theory).

mp: 99° C.

$^1$H-NMR (DMSO-d6, 300 Mz) δ (ppm)=2.29 (s, CH$_3$, 3H), 3.10-3.25 (m, CH$_2$N, 2H), 3.74-3.87 (m, CH, CH$_2$, 2H), 3.98 (dd, CH$_2$, 1H, J 10.2 Hz, J 3.2 Hz), 7.17 (d, CH, 1H, J 4.0 Hz), 7.42 (d, CH, 1H, J 9.1 Hz), 7.58 (d, CH, 1H, J 4.0 Hz), 7.75 (d, CH, 1H, J 9.1 Hz), 8.58 (t. NH, 1H, J 5.8 Hz).

$^{13}$C-NMR (DMSO-d6, 300 Mz) δ (ppm)=22.12, 43.02, 69.24, 70.97, 127.62, 128.39, 130.52, 132.50, 136.52, 136.87, 139.31, 145.90, 163.11.

Example 3

4-[4-[(5R)-5-(Chlorothiopheno-2-carboxylic acid ((S)-2-hydroxy-3-tosyloxy)-propyl)-amide

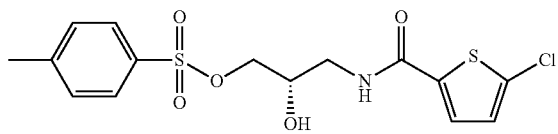 [SMILES: Cc1ccc(S(=O)(=O)OC[C@@H](O)CNC(=O)c2ccc(Cl)s2)cc1]

5.00 g of 4-[4-[(5R)-5-(chlorothiopheno-2-carboxylic acid (S)-2,3-dihydroxy-propylamide (MW=235.69; 1 eq.) was dissolved in 100 mL of pyridine and cooled to −10° C. Then 4.04 g of tosylchloride (MW=190.65; 1 eq.) were added. After stirring for 20 hours at this temperature 400 mL of methylene chloride and 400 mL of water were added to the reaction mixture and the pH was adjusted to 2.0 by addition of 6 M hydrochloric acid. After separation of the layers, the aqueous layer was extracted once more with 100 mL of methylene chloride. The combined organic layers were washed with 100 mL of water and dried over sodium sulfate. Then the solution was concentrated in vacuo at room temperature to afford 6.90 g of the title compound in the form of an oil.

Purity (HPLC): 84.3%

Example 4

5-Chlorothiophen-2-carboxylic acid-{(R)-2-hydroxy-3-[4-(3-oxomorpholin-4-yl)phenylamino]-propyl}amide

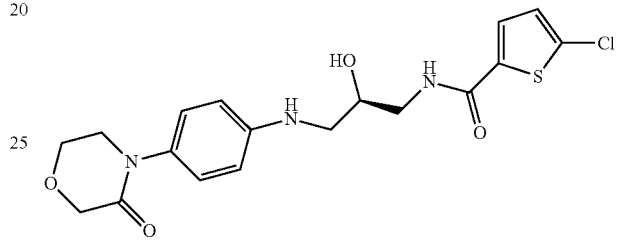

To a suspension of 2.55 g of 4-[4-[(5R)-5-(chlorothiopheno-2-carboxylic acid ((S)-2-hydroxy-3-tosyloxy)-propyl)-amide (MW=389.88; 1 eq.) in 15 mL toluene were added 1.22 g of 4-(4-amino-phenyl)-morpholin-3-one (MW=190.22; 1 eq.), 0.73 g collidine (MW=121.18; 0.9 eq.) and 0.29 mL ethanol. The reaction mixture was heated to 105° C. and stirred at this temperature for 3 hours. Then 2.5 mL of n-butanol were added and the mixture was cooled to 22° C. After stirring for at least 1 hour at ambient temperature the product was isolated by filtration and washed with toluene and water. The wet product was dried at 30° C. in vacuo to yield 2.00 g of the title compound (76% by theory).

Example 5

5-Chloro-N-({(5S)-2-oxo-3-[4-(3-oxo-4-morpholinyl)phenyl]-1,3-oxazolidin-5-yl}methyl)-2-thiophen-carboxamide

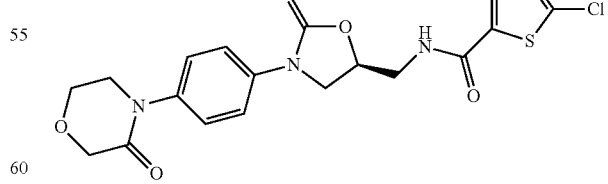

Under an atmosphere of nitrogen to a suspension of 14.85 g of 5-chlorothiophen-2-carboxylic acid-{(R)-2-hydroxy-3-[4-(3-oxomorpholin-4-yl)phenylamino]propyl}amide (MW=409.89; 1 eq.) in 145 mL toluene and 22 mL N-methylpyrrolidone were added 7.13 g (MW=162.15; 1.2 eq.) of 1,1'-carbonyldiimidazol. The reaction mixture was heated to 80° C. After stirring for 30 minutes the mixture was heated to 110° C. and stirred at this temperature for 2 hours. Then the mixture was cooled to 22° C. After stirring for 1 hour at ambient temperature the product was isolated by filtration and washed with 60 mL of toluene and 60 mL of water. The wet product was dried at 30° C. in vacuo to yield 15.99 g (MW=435.89; 1.013 eq.) of the title compound (90% of theory).

$^{13}$C-NMR (DMSO-d6, 300 Mz) δ (ppm)=49.98, 64.34, 68.59, 70.16, 70.80, 119.34, 126.81, 128.49, 128.92, 129.15, 131.02, 132.52, 134.03, 137.08, 137.94, 139.31, 145.99, 153.23, 161.42, 166.76.

Example 7

5-Chloro-N-({(5S)-2-oxo-3-[4-(3-oxo-4-morpholinyl)phenyl]-1,3-oxazolidin-5-yl}methyl)-2-thiophen-carboxamide

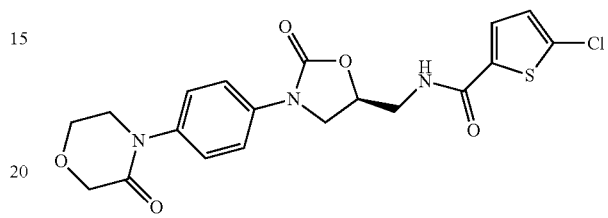

Under an atmosphere of nitrogen a suspension of 1.00 g of toluene-4-sulfonic acid (S)-3-[(5-chloro-thiophene-2-carbonyl)-amino]-2-[4-(3-oxo-morpholin-4-yl)-phenylcarbamoyloxy]-propyl ester (MW=608.09; 1 eq.) in 25 mL tetrahydrofuran was cooled to 0° C. At this temperature 1.6 mL of a 1M solution of lithium t-butoxide in tetrahydrofuran were added dropwise. After stirring at this temperature for 1 hour the resulting slurry was filtered. The cake was rinsed with 14 mL of tetrahydrofuran and 14 mL of water. The wet product was dried at 30° C. in vacuo to yield 0.63 g (MW=435.89; 1.013 eq.) of the title compound (88.5% of theory).

Example 6

Toluene-4-sulfonic acid (S)-3-[(5-chloro-thiophene-2-carbonyl)-amino]-2-[4-(3-oxo-morpholin-4-yl)-phenylcarbamoyloxy]-propyl ester

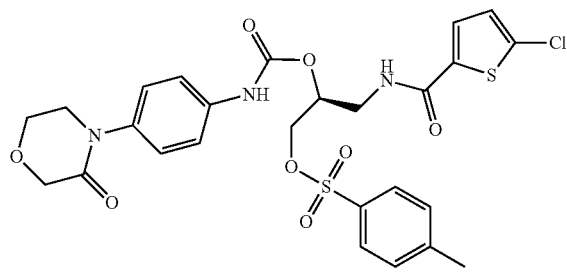 [SMILES: Cc1ccc(S(=O)(=O)OC[C@H](CNC(=O)c2ccc(Cl)s2)OC(=O)Nc2ccc(N3CCOCC3=O)cc2)cc1]

Under an atmosphere of nitrogen to a suspension of 20.0 g of 4-[4-[(5R)-5-(chlorothiopheno-2-carboxylic acid ((S)-2-hydroxy-3-tosyloxy)-propyl)-amide (MW=389.88; 1 eq.) in 400 mL of methylene chloride were added at 10° C. 12.2 g of pyridine (MW=79.10; 3 eq.) and 5.1 g of bis(trichloromethyl)carbonate (MW=296.75; 0.34 eq.). After stirring for 15 minutes 10.0 g of 4-(4-amino-phenyl)-morpholin-3-one (MW=192.22; 1 eq.), 4.1 g pyridine (MW=79.10; 1 eq.) and 0.19 g dimethylaminopyridine were added. The reaction mixture was allowed to warm to 22° C. After stirring for 75 minutes at this temperature the reaction was quenched by addition to a mixture of 2 L of a saturated aqueous solution of ammonium chloride and 1 L of methylene chloride. Then the organic layer was separated and the aqueous layer was extracted once more with 400 mL of methylene chloride. The combined methylene chloride layers were washed with 400 mL of water, dried with sodium sulfate and concentrated in vacuo to a weight of 86 g. The concentrate was dissolved in 200 mL of acetonitrile at 40° C. and then allowed to cool to ambient temperature. The resulting slurry was stirred for 1 hour at ambient temperature and cooled to 0° C. After stirring for 2 hours at this temperature the suspension was filtered and the filter cake was washed with 50 mL of acetonitrile. The wet product was dried at 30° C. in vacuo to yield 21.1 g of the title compound in form of crystalline powder (78% by theory).

mp: 142° C.

$^{1}$H-NMR (DMSO-d6, 300 Mz) δ (ppm)=2.29 (s, CH$_3$, 3H), 3.49 (m, CH$_2$N, 2H), 3.68 (m, CH$_2$, 2H), 3.95 (m, CH$_2$, 2H), 4.18 (s, CH$_2$CO, 2H), 4.18-4.32 (m, CH$_2$, 2H), 5.07 (m, CH, 1H), 7.18 (d, J=1.9 Hz, CH, 1H), 7.22-7.48 (m, CH, 6H), 7.59 (d, J=3.9 Hz, CH, 1H), 7.77 (d, J=1.9 Hz, CH, 1H), 8.75 (t. J 5.1 Hz, NH, 1H), 9.81 (s, NH, 1H).

Example 8

4-(Isocyanato-phenyl)-morpholin-3-one

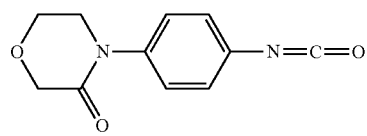 [SMILES: O=C=Nc1ccc(N2CCOCC2=O)cc1]

Under an atmosphere of nitrogen to a suspension of 25.9 g of 4-(4-amino-phenyl)-morpholin-3-one (APMO) (MW=192.22; 1 eq.) and 27.2 g of triethylamine (MW=101.19; 2 eq.) in 390 mL of methylene chloride was added at room temperature a solution of 14.6 g chloroformic acid trichloromethyl ester (MW=197.83; 0.55 eq.) in 390 mL of methylene chloride within 10 minutes. The reaction was slight exothermic and the temperature rose to 35° C. After stirring at room temperature for two hours the resulting suspension was filtered and the filtrate was concentrated in vacuo at 45° C. to afford 49.5 g of the title compound. The resulting material was used in the following step without further purification.

mp: 119° C.

$^{1}$H-NMR (CD$_3$CN, 300 Mz) δ (ppm)=3.71 (m, CH$_2$O, 2H), 3.00 (m, CH$_2$N, 2H), 3.92 (m, CH$_2$, 2H), 4.21 (s, CH$_2$CO, 2H), 7.21 and 7.37 (m, CH, 4H).

$^{13}$C-NMR (CD$_3$CN, 300 Mz) δ (ppm)=45.97, 49.70, 64.15, 68.36, 115.12, 125.65, 127.27, 132.00, 140.01, 166.86.

Example 9

5-Chloro-N-({(5S)-2-oxo-3-[4-(3-oxo-4-morpholinyl)phenyl]-1,3-oxazolidin-5-yl}methyl)-2-thiophencarboxamide

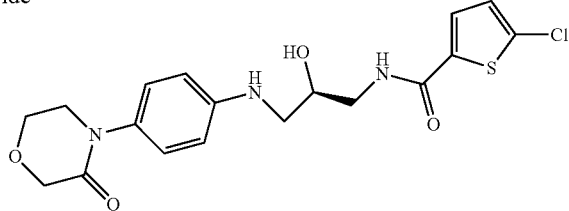

Under an atmosphere of nitrogen 25 mg of LiBr and 63 mg of tributylphosphinoxide were added to 5 mL of toluene and the mixture was heated to reflux. At this temperature 1.09 g of 4-(isocyanato-phenyl)-morpholin-3-one (MW=218.21; 1 eq.) and 1.09 g 5-chloro-thiophene-2-carboxylic acid ((S)-1-oxiranylmethyl)-amide (MW=217.68; 1 eq.) were added and the mixture was refluxed for 3 hours. After stirring for 3 hours the product was isolated by filtration and washed with toluene and water. The wet product was dried at 30° C. in vacuo to yield 1.20 g (MW=435.89; 1.013 eq.) of the title compound (55% of theory).

Example 10

5-Chloro-thiophene-2-carboxylic acid ((S)-1-oxiranylmethyl)-amide

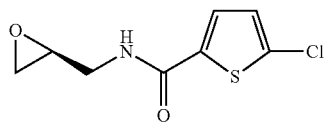 [SMILES: O=C(NC[C@H]1CO1)c1ccc(Cl)s1]

12.6 g of powdered potassium carbonate (MW=138.21; 4.3 eq.) were added to a solution of 5.00 g of 4-[4-[(5R)-5-(chlorothiopheno-2-carboxylic acid ((S)-2-hydroxy-3-tosyloxy)-propyl]-amide (MW=389.88; 1 eq.) in 250 mL of methylene chloride under an atmosphere of nitrogen. The reaction mixture was stirred at room temperature for 3 days. Then the suspension was filtered and the filter cake was washed with methylene chloride. Filtrate and wash liquid were combined and concentrated in vacuo at room temperature to afford 2.74 g of the title compound. The resulting material was used in the following step without further purification.

Example 11

5-Chloro-N-({(5S)-2-oxo-3-[4-(3-oxo-4-morpholinyl)phenyl]-1,3-oxazolidin-5-yl}methyl)-2-thiophencarboxamide

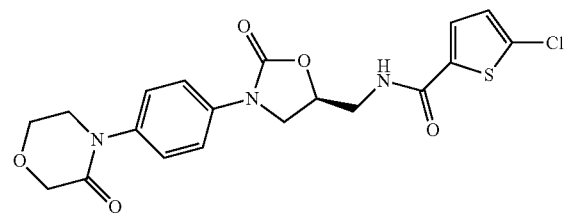 [SMILES: O=C(NC[C@H]1CN(c2ccc(N3CCOCC3=O)cc2)C(=O)O1)c1ccc(Cl)s1]

A mixture of 4.2 mL of acetic acid anhydride and 3.0 mL of pyridine was cooled to 0° C. At this temperature 4.00 g of 4-[4-[(5R)-5-(chlorothiopheno-2-carboxylic acid ((S)-2-hydroxy-3-tosyloxy)-propyl)-amide (MW=389.88; 1 eq.) were added. After stirring for 1 hour at this temperature the reaction mixture was poured into 150 mL of methyl-t-butylether and 50 mL of water and the pH was adjusted to 2.0 by addition of 6 M hydrochloric acid. After separation of the layers, the aqueous layer was extracted once more with 50 mL of methyl-t-butylether. The combined organic layers were washed with 50 mL of saturated bicarbonate and brine and dried over sodium sulfate. The solution was concentrated to dryness in vacuo at room temperature. The residue was dissolved in 20 mL of acetonitrile and then 2.48 g of 4-(3-oxo-morpholin-4-yl)-phenyl]-carbamic acid benzyl ester (MW=326.36; 0.76 eq.) and 302 μL of methanol (MW=32.04; 0.76 eq.) were added. The mixture was cooled to 0° C. and 1.22 g of lithium tert.-butoxide were added. After stirring for 17 hours at 0° C., the resulting suspension was filtered. The filter cake was washed with acetonitrile and water. The wet product was dried at 30° C. in vacuo to yield 0.94 g (MW=435.89) of the title compound (21.1% of theory).

Example 12

[4-(3-Oxo-morpholin-4-yl)-phenyl]-carbamic acid benzyl ester

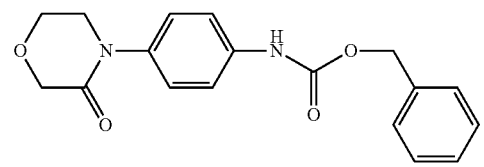 [SMILES: O=C(Nc1ccc(N2CCOCC2=O)cc1)OCc1ccccc1]

3.17 g of sodium bicarbonate (MW=84.01; 2.1 eq.) and then 3.28 g of benzyl chloroformate (MW=170.60; 1.03 eq.) were added to a solution of 3.53 g of APMO (MW=192.22; 1 eq.) in 68 mL of acetone and 34 mL of water at 0° C. over 5 min via syringe. The reaction mixture was stirred for two hours and then poured onto 110 mL of water. After stirring for 1.5 hours at 0° C. the resulting suspension was filtered and the filter cake washed with 100 mL of water. The wet product was dried at 30° C. in vacuo to yield 5.76 g (MW=326.36) of the title compound (96.2% of theory).

The invention claimed is:

1. Method for the preparation of the compound having the formula (V)

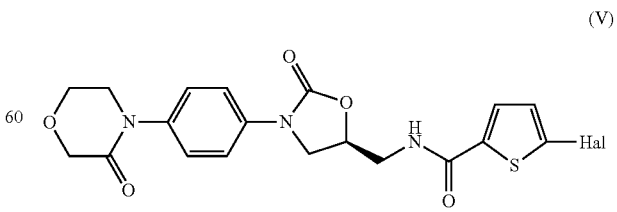

(V)

wherein Hal is a halogen atom or a pseudohalogen comprising converting a compound having the formula (II)

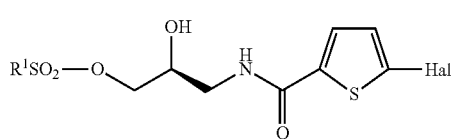
(II)

to the compound of formula (V), wherein R¹ is selected from the group consisting of $C_{1-4}$ alkyl groups and a phenyl group optionally substituted with a $C_{1-4}$ alkyl group.

2. The method according to claim 1, wherein R¹ is selected from methyl, phenyl and tolyl.

3. A method for the preparation of a compound having the formula (V)

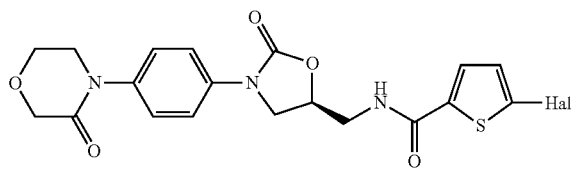
(V)

wherein Hal is a halogen atom or a pseudohalogen;

wherein the method comprises reacting (i) a compound having the formula (II)

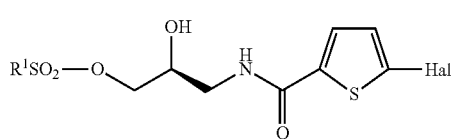
(II)

wherein R¹ is selected from the group consisting of $C_{1-4}$ alkyl groups and a phenyl group optionally substituted with a $C_{1-4}$ alkyl group; and Hal is a halogen atom or a pseudohalogen;

(ii) a compound having the formula (III)

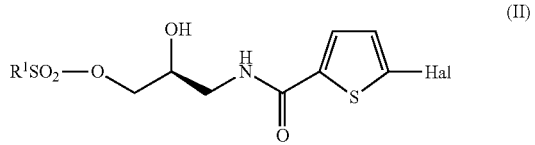
(III)

and (iii) phosgene or an equivalent thereof.

4. The method according to claim 3, wherein the compound having the formula (II) is first reacted with a compound having the formula (III) to obtain a compound having the formula (VI)

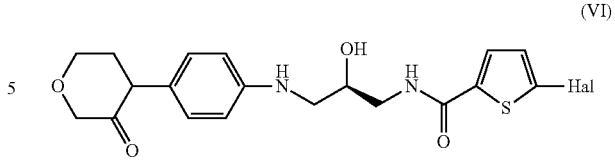
(VI)

wherein Hal is a halogen atom or a pseudohalogen;

and the compound having the formula (VI) is subsequently reacted with phosgene or an equivalent thereof to obtain the compound having the formula (V).

5. The method according to claim 3, wherein the compound having the formula (II) is first reacted with phosgene or an equivalent thereof; the reaction product thereof is subsequently reacted with a compound having the formula (III) to obtain a compound having the formula (IV)

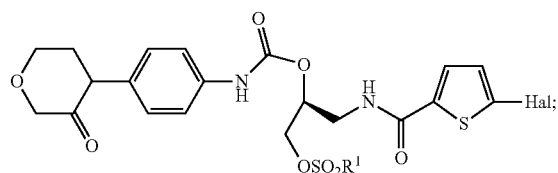
(IV)

wherein R¹ is selected from the group consisting of $C_{1-4}$ alkyl groups and a phenyl group optionally substituted with a $C_{1-4}$ alkyl group; and Hal is a halogen atom or a pseudohalogen;

and the compound having the formula (IV) is converted to the compound having the formula (V).

6. The method according to claim 1, wherein the compound having the formula (II) is prepared from a compound having the formula (I)

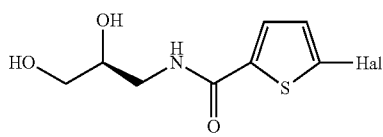
(I)

wherein Hal is a halogen atom or a pseudohalogen.

7. A method for preparing a compound having the formula (II)

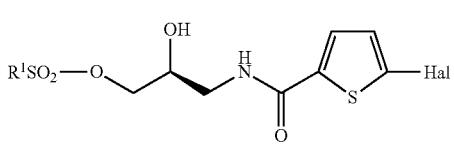
(II)

wherein R¹ is selected from the group consisting of $C_{1-4}$ alkyl groups and a phenyl group optionally substituted with a $C_{1-4}$ alkyl group and Hal is a halogen atom or a pseudohalogen;

wherein a compound having the formula (I)

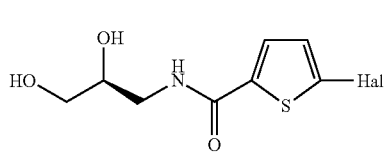

wherein Hal is a halogen atom or a pseudohalogen;
is converted to the compound having the formula (II) by reacting the compound having the formula (I) with a compound having the formula R¹SO₂X.

8. A method for preparing a compound having the formula (VI)

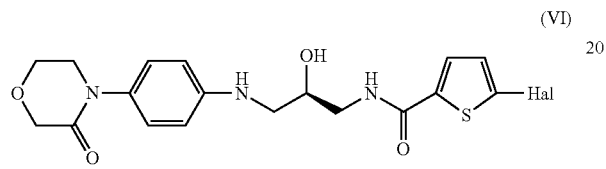

wherein Hal is a halogen atom or a pseudohalogen;
wherein a compound having the formula (II)

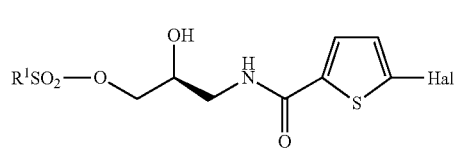

wherein $R^1$ is selected from the group consisting of $C_{1-4}$ alkyl groups and a phenyl group optionally substituted with a $C_{1-4}$ alkyl group; and Hal is a halogen atom or a pseudohalogen;
is reacted with a compound having the formula (III)

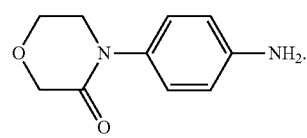

9. A method for preparing a compound having the formula (IV)

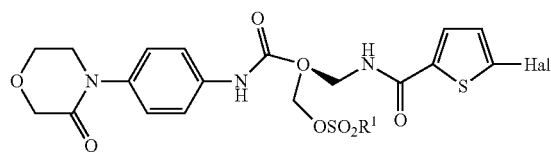

wherein $R^1$ is selected from the group consisting of $C_{1-4}$ alkyl groups and a phenyl group optionally substituted with a $C_{1-4}$ alkyl group; and Hal is a halogen atom or a pseudohalogen;

wherein a compound having the formula (II)

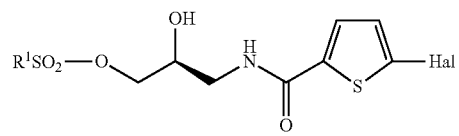

wherein $R^1$ is selected from the group consisting of $C_{1-4}$ alkyl groups and a phenyl group optionally substituted with a $C_{1-4}$ alkyl group; and Hal is a halogen atom or a pseudohalogen;
is first reacted with phosgene or an equivalent thereof and the reaction product thereof is subsequently reacted with a compound having the formula (III)

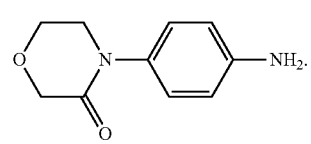

10. A method for preparing a compound having the formula (V)

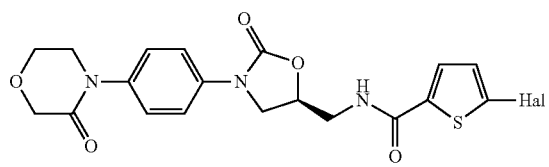

wherein Hal is a halogen atom or a pseudohalogen;
wherein a compound having the formula (IV)

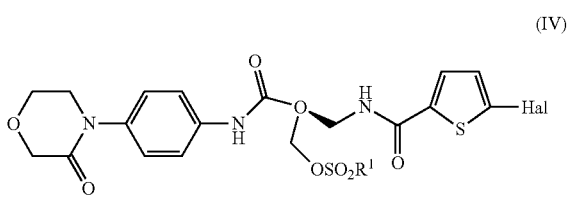

wherein $R^1$ is selected from the group consisting of $C_{1-4}$ alkyl groups and a phenyl group optionally substituted with a $C_{1-4}$ alkyl group; and Hal is a halogen atom or a pseudohalogen;
is converted to the compound having the formula (V) by performing a cyclization reaction.

11. A method for preparing a compound having the formula (V)

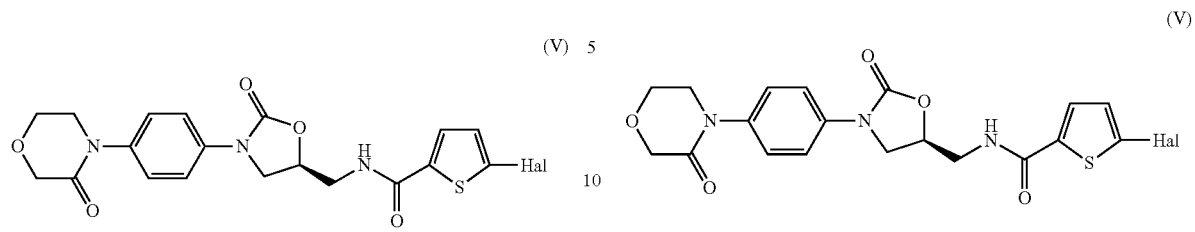

wherein Hal is a halogen atom or a pseudohalogen;
wherein a compound having the formula (II)

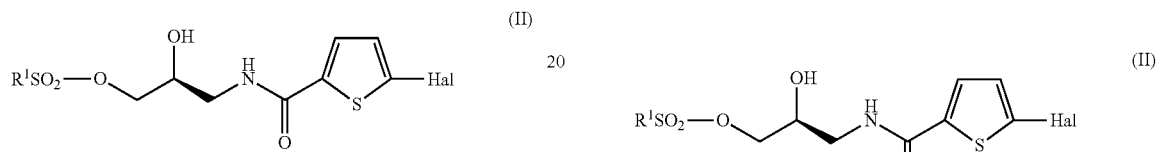

wherein $R^1$ is selected from the group consisting of $C_{1-4}$ alkyl groups and a phenyl group optionally substituted with a $C_{1-4}$ alkyl group; and Hal is a halogen atom or a pseudohalogen;
is reacted with a compound having the formula (VIII)

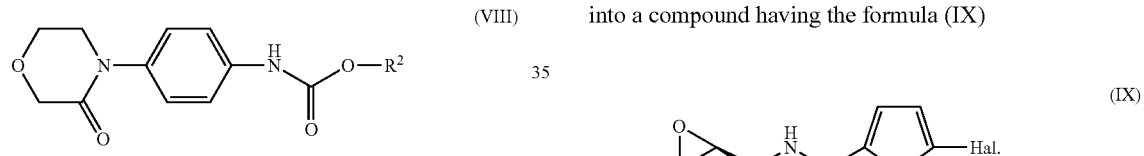

wherein $R^2$ is a $C_{1-6}$ alkyl group or a benzyl group.

12. A method comprising the step of reacting a compound having the formula (II)

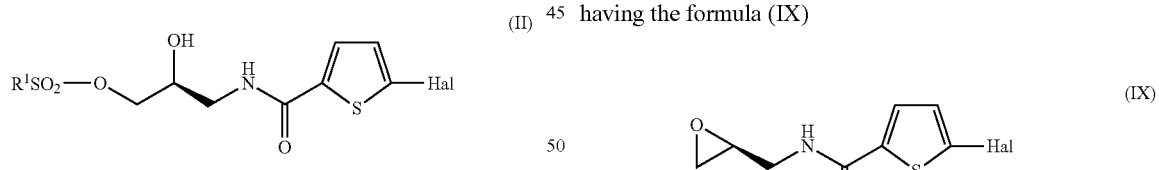

wherein $R^1$ is selected from the group consisting of $C_{1-4}$ alkyl groups and a phenyl group optionally substituted with a $C_{1-4}$ alkyl group; and Hal is a halogen atom or a pseudohalogen;
with a compound having the formula (VII)

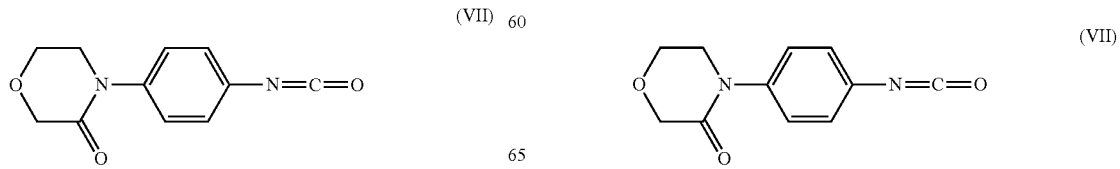

to provide a compound having the formula (V)

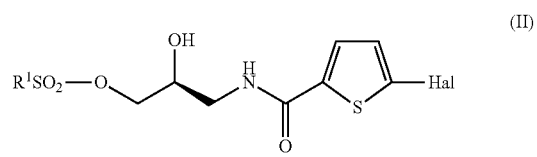

wherein Hal is a halogen atom or a pseudohalogen.

13. A method comprising the step of converting a compound having the formula (II)

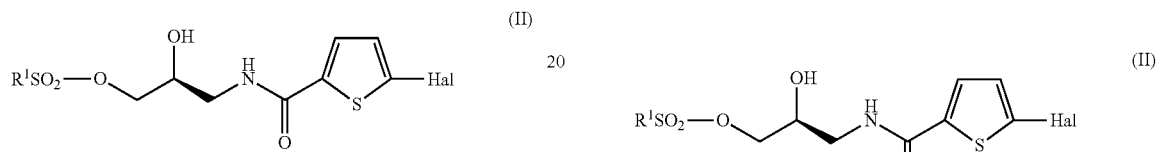

wherein $R^1$ is selected from the group consisting of $C_{1-4}$ alkyl groups and a phenyl group optionally substituted with a $C_{1-4}$ alkyl group; and Hal is a halogen atom or a pseudohalogen;
into a compound having the formula (IX)

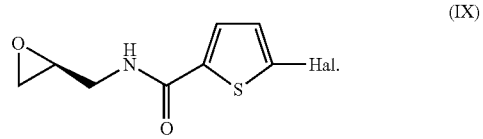

14. A method comprising the step of reacting a compound having the formula (IX)

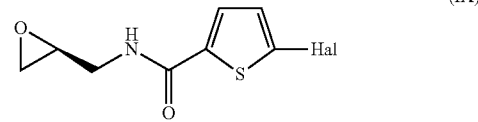

wherein Hal is a halogen atom or a pseudohalogen;
with a compound having the formula (VII)

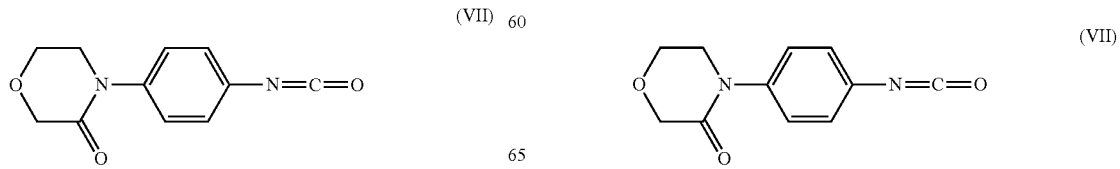

to obtain a compound having the formula (V)

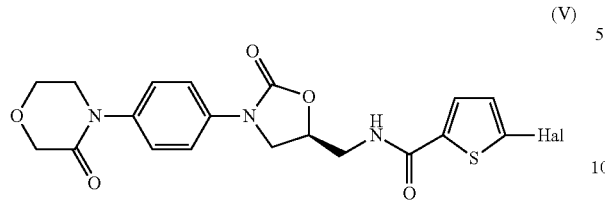

wherein Hal is a halogen atom or a pseudohalogen.

15. A compound selected from the group consisting of:

a compound having the formula (II)

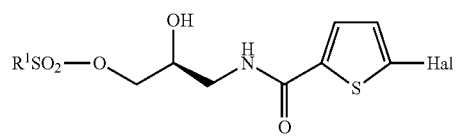

wherein $R^1$ is selected from the group consisting of $C_{1-4}$ alkyl groups and a phenyl group optionally substituted with a $C_{1-4}$ alkyl group; and Hal is a halogen atom or a pseudohalogen;

(ii) a compound having the formula (IV)

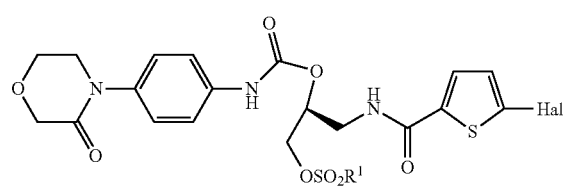

wherein $R^1$ is selected from the group consisting of $C_{1-4}$ alkyl groups and a phenyl group optionally substituted with a $C_{1-4}$ alkyl group; and Hal is a halogen atom or a pseudohalogen;

(iii) a compound having the formula (VII)

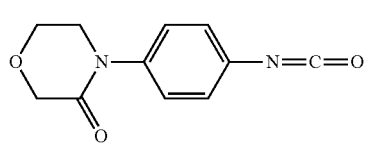

and
(iv) a compound having the formula (IX)

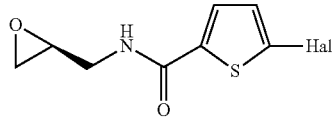

wherein Hal is a pseudohalogen.

16. The method according to claim 2, wherein the compound having the formula (II) is prepared from a compound having the formula (I)

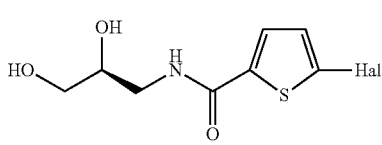

wherein Hal is a halogen atom or a pseudohalogen.

17. The method of claim 3, wherein the compound having the formula (II) is prepared from a compound having the formula (I)

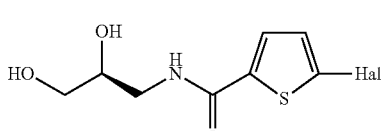

wherein Hal is a halogen atom or a pseudohalogen.

18. The method of claim 4, wherein the compound having the formula (II) is prepared from a compound having the formula (I)

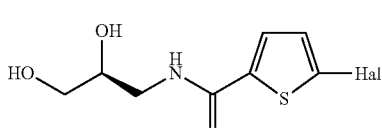

wherein Hal is a halogen atom or a pseudohalogen.

19. The method of claim 5, wherein the compound having the formula (II) is prepared from a compound having the formula (I)

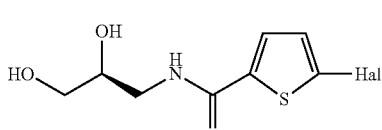

wherein Hal is a halogen atom or a pseudohalogen.

* * * * *

UNITED STATES PATENT AND TRADEMARK OFFICE
CERTIFICATE OF CORRECTION

PATENT NO. : 8,648,189 B2  
APPLICATION NO. : 13/577441  
DATED : February 11, 2014  
INVENTOR(S) : Hubert Sturm et al.

Page 1 of 1

It is certified that error appears in the above-identified patent and that said Letters Patent is hereby corrected as shown below:

On the Title Page, in the Title (54) and in the Specification, Column 1, Line 2, delete "RIVORAXABAN" and insert --RIVAROXABAN-- therefor.

Signed and Sealed this  
Twelfth Day of May, 2015

Michelle K. Lee  
*Director of the United States Patent and Trademark Office*